(12) United States Patent
Wilson et al.

(10) Patent No.: US 6,475,769 B1
(45) Date of Patent: Nov. 5, 2002

(54) METHODS AND CELL LINE USEFUL FOR PRODUCTION OF RECOMBINANT ADENO-ASSOCIATED VIRUSES

(75) Inventors: James M. Wilson, Gladwyne, PA (US); Guangping Gao, Rosemont, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/528,017

(22) Filed: Mar. 17, 2000

Related U.S. Application Data

(63) Continuation of application No. PCT/US98/19463, filed on Sep. 18, 1998.
(60) Provisional application No. 60/059,340, filed on Sep. 19, 1997.

(51) Int. Cl.$^7$ .................................................. C12N 7/00
(52) U.S. Cl. ................................ 435/235.1; 435/320.1; 435/326; 435/366; 435/367; 536/23.72
(58) Field of Search ................................. 435/369, 367, 435/320.1, 235.1, 325, 366; 536/23.72

(56) References Cited

U.S. PATENT DOCUMENTS

| | | | | |
|---|---|---|---|---|
| 5,622,856 A | * | 4/1997 | Natsoulis | 435/325 |
| 5,658,785 A | | 8/1997 | Johnson | 435/367 |

FOREIGN PATENT DOCUMENTS

| | | |
|---|---|---|
| WO | WO 96/13598 | 5/1996 |
| WO | WO 96/17947 | 6/1996 |
| WO | WO 97/06272 | 2/1997 |

OTHER PUBLICATIONS

K. Tamayose et al., "A New Strategy for Large–Scale Preparation of High–Titer Recombinant Adeno–Associated Virus Vectors by Using Packaging Cell Lines and Sulfonated Cellulose column Chromatography," *Hum. Gene Ther.,* 7:507–513 (Mar. 1, 1996).
Q. Yang et al., "Characterization of Cell Lines that Inducibly Express the Adeno–Associated Virus Rep Proteins", *J. Virol.,* 68:4847–4856 (Aug. 1994).
K.R. Clark et al., "Cell Lines for the Production of Recombinant Adeno–Associatd Virus," *Hum. Gene Ther.,* 6(10):1329:1341 (Oct. 1995) XP000569718.
K.R. Clark et al., "A Stable Cell Line Carrying Adenovirus–Inducible REP and CAP Genes Allows for Infectivity Titration of Adeno–Associated Virus Vectors", *Gene Ther.,* 3:1124–1132 (Dec. 1996) XP0002064828.
M. Mamounas et al., "Increased Titer of Recombinant AAV Vectors by Gene Transfer with Adenovirus Coupled to DNA–polylysine Complexes", *Gene Ther.,* 2:429–432 (Aug. 1995).
T.R. Flotte et al., "An Improved System for Packaging Recombinant Adeno–Associated Virus Vectors Capable of In Vivo Transduction," *Gene Ther.,* 2:29–37 (Jan. 1995) XP000609327.
G–P. Gao et al., "High Titer Adeno–Associated Viral Vectors from a Rep/Cap Cell Line and Hybrid Shuttle Virus", *Hum. Gene Ther.,* 9:2353–2362 (Nov. 1, 1998).
B. J. Carter, in "Handbook of Parvoviruses", ed., P. Tijsser, CRC Press, pp. 155–168 (1990).
R.M. Kotin et al., "Site–Specific Integration by Adeno–Associated Virus," *Proc. Natl. Acad. Sci USA,* 87: 2211–2215 (Mar. 1990).
R.J. Samulski et al., "Targeted Integration of Adeno–Associated Virus (AAV) into Human," *EMBO J.,* 10:3941–3950 (Dec. 1991).
R.J. Samulski et al., "A Recombinant Plasmid from Which an Infectious Adeno–Associated Virus Genome Can Be Excised In vitro and Its Use to Study Viral Replication," *J. Virol.,* 61(10):3096–3101 (Oct. 1987).
F.K. Ferrari et al., "New Developments in the Generation of Ad–Free–, High–titer rAAV Gene Therapy Vectors", *Nature Med.,* 3(11):1295–1297 (Nov. 1997).
K.J. Fisher et al., "Transduction with Recombinant Adeno–Associated Virus for Gene Therapy is Limited by Leading–Strand Synthesis", *J. Virol.,* 70:520–532 (Jan. 1996).
R.M. Kotin, "Prospects for the Use of Adeno–Associated Virus as a Vector for Human Gene Therapy," *Hum. Gene Ther.,* 5:793–801 (Jul. 1994).

\* cited by examiner

*Primary Examiner*—Laurie Scheiner
(74) *Attorney, Agent, or Firm*—Howson and Howson

(57) ABSTRACT

Methods for efficient production of recombinant AAV employ a host cell which comprising AAV rep and cap genes stably integrated within the cell's chromosomes, wherein the AAV rep and cap genes are each operatively linked to regulatory sequences capable of directing the expression of the rep and cap gene products upon infection of the cell with a helper virus, a helper gene, and a helper gene product. A method for producing recombinant adeno-associated virus (rAAV) involves infecting such a host cell with a helper virus, gene or gene product and infecting the infected host cell with a recombinant hybrid virus or plasmid vector containing adenovirus cis-elements necessary for replication and virion encapsidation, AAV sequences comprising the 5' and 3' ITRs of an AAV, and a selected gene operatively linked to regulatory sequences directing its expression, which is flanked by the above-mentioned AAV sequences.

8 Claims, 3 Drawing Sheets

METHODS AND CELL LINE USEFUL FOR PRODUCTION OF RECOMBINANT ADENO-ASSOCIATED VIRUSES

CROSS-REFERENCE TO RELATED APPLICATIONS

This is a continuation of International Patent Application No. PCT/US98/19463, filed on Sep. 18, 1998, which claims the benefit of the priority of U.S. patent application Ser. No. 60/059,340, filed on Sep. 19, 1997.

This invention was made with financial assistance from the National Institutes of Health Grant Nos. NIAMS P01AR/MS43648, P30 DK47757-05, P01 HD32649-04, P01 AR/NS43648-03, and P01 CA66726-03. The United States government has certain rights in this invention.

BACKGROUND OF THE INVENTION

Adeno-associated virus (AAV) is a replication-deficient human parvovirus, the genome of which is about 4.6 kb in length, including 145 nucleotide inverted terminal repeats (ITRs). Two open reading frames encode a series of rep and cap polypeptides. Rep polypeptides (rep78, rep68, rep62 and rep40) are involved in replication, rescue and integration of the AAV genome. The cap proteins (VP 1, VP2 and VP3) form the virion capsid. Flanking the rep and cap open reading frames at the 5' and 3' ends are 145 bp inverted terminal repeats (ITRs), the first 125 bp of which are capable of forming Y- or T-shaped duplex structures. Of importance for the development of AAV vectors, the entire rep and cap domains can be excised and replaced with a therapeutic or reporter transgene [B. J. Carter, in "Handbook of Parvoviruses", ed., P. Tijsser, CRC Press, pp.155–168 (1990)]. It has been shown that the ITRs represent the minimal sequence required for rescue, packaging, and integration of the AAV genome.

The wild type, nonpathogenic human virus is capable of infecting a wide variety of cells and establishing a latent infection of the cell via a provirus that integrates at high frequency into a specific region of chromosome 19 [Kotin, R. M. et al, *Proc. Natl. Acad Sci. USA* 87, 2211–2215 (1990); Samulski, R. J. et al. *EMBO J.* 10, 3941–3950 (1991)]. Production of infectious virus and replication of the virus does not occur unless the cell is coinfected with a helper virus, such as adenovirus or herpesvirus. Upon infection with a helper virus, the genes of latent AAV (i.e., rep and cap) are activated, resulting in rescue of the AAV provirus, replication of the AAV genome, and formation of AAV virions, as well as generation of additional helper virus. The infecting parental ssDNA is expanded to duplex replicating form (RF) DNAs in a rep dependent manner. The rescued AAV genomes are packaged into preformed protein capsids (icosahedral symmetry approximately 20 nm in diameter) and released as infectious virions that have packaged either +or –ss DNA genomes following cell lysis.

AAV possesses unique features that make it attractive as a vector for delivering foreign DNA to cells. Progress towards establishing AAV as a transducing vector for gene therapy has been slow. Evaluation of recombinant AAV (rAAV) produced recombinantly and exclusive of wildtype AAV reformed by recombinant methods in preclinical models of gene therapy has been limited for a variety of reasons, primarily because methods of production are inefficient and often generate substantial quantities of replication competent AAV. Replication defective forms of AAV are created by transfecting vector DNA (transgene flanked by AAV ITRs) together with a rep/cap expressing plasmid concurrent with adenovirus infection [Samulski, R. et al, *J. Virol*, 61(10):3096–3101 (1987)] or transfection with an adenovirus helper plasmid [Ferrari, F. K. et al, *Nature Med*, 3, 1295–1297 (1997)]. The standard method, based on transient transfection, is not easily scaled-up, making it difficult to obtain virus [Fisher, K. J. et al. *J. Virol*. 70, 520–532 (1996)]. Furthermore, preparations are invariably contaminated with replication competent AAV (rcAAV) formed by, for example, nonhomologous recombination, during the process of transfection. Another method for producing rAAV has been described based on the simultaneous transient transfection of cis and trans plasmids together with an adenovirus helper plasmid [Ferrari et al, *Nature Med*. 3: 1295–1297 (1997)]. This approach has the advantage of minimizing contaminating adenovirus but suffers from the creation of rcAAV and difficulties in scaling-up. A specific obstacle to the use of AAV for delivery of DNA, especially for therapeutic applications, has been lack of highly efficient schemes for encapsidation of recombinant genomes and production of infectious virions [R. Kotin, *Hum. Gene Ther.*, 5:793–801 (1994)].

Problems exist in attempts to improve AAV production including the use of cell lines stably expressing vector and/or rep/cap. Creation of a cell line stably expressing rep and cap has been difficult because of cellular toxicity of rep gene products. Several cell lines previously described do not express sufficient quantities of rep or cap to sustain high titer production of vector [Tamayose, K. et al, *Hum. Gene Thera*. 7, 507–513 (1996); Yang, Q., et al, *J. Virol*. 68, 4847–4856 (1994); see, also, Clark, K. R. et al, *Hum. Gene Thera*. 6, 1329–1341 (1995) and U.S. Pat. No. 5,658,785]. Other strategies have been described that provide more efficient ways to transiently express and regulate rep and cap [Mamounas, M., et al, *Gene Thera*. 2, 429–432 (1995); and Flotte, T. R. et al. *Gene Thera*. 2, 29–37 (1995)].

Disadvantages of current methods for production of rAAV that employ transfection of rAAV genome into host cells followed by co-infection with wild-type AAV and adenovirus, include the production of unacceptably high levels of wild-type AAV, little recombinant gene expression and inefficient integration. Another recognized means for manufacturing transducing AAV virions entails co-transfection with two different, yet complementing plasmids. One of these plasmids contains a therapeutic or reporter transgene flanked (sandwiched) between the two cis acting AAV ITRs. The AAV components that are needed for rescue and subsequent packaging of progeny recombinant genomes are provided in trans by a second plasmid encoding the viral open reading frames for rep and cap proteins. However, both rep and cap are toxic to the host cells. This toxicity has been the major source of difficulty in providing these genes in trans for the construction of a useful rAAV gene therapy vector.

There remains a need in the art for additional methods permitting the efficient production of AAV and recombinant AAV viruses for use as vectors for somatic gene therapy at high titers not previously achieved.

SUMMARY OF THE INVENTION

The present invention provides a novel method and a novel cell line which permits efficient and high level production of recombinant adeno-associated virus (rAAV) as described in detail below, and produces rAAV essentially free of replication competent AAV (rcAAV).

In one aspect, the invention provides a cell comprising an AAV rep gene and an AAV cap gene stably integrated within the cell's chromosomes, wherein the AAV rep and cap genes are operatively linked to regulatory sequences capable of directing the expression of the rep and cap genes, and wherein the cell expresses gene products of the rep and cap genes upon introduction to the cell of a helper. The helper is a helper virus, a helper gene, or a helper gene product. The cell lines of this invention are characterized by integration of multiple copies of promoter-rep-cap gene cassettes in a concatamer form into the host chromosome. The cell lines of this invention are also characterized by providing high level expression of rAAV (e.g., greater than $1 \times 10^3$ rAAV particles per cell) upon the introduction of the helper to the cell line in comparison to the yields of rAAV from other stably rep/cap transfected cells. One embodiment of this cell is a host cell derived from HeLa cells, B-50 [ATCC Accession No. CRL-12401] which stably expresses AAV rep and cap genes under the control of the endogenous AAV p5 promoter.

In another aspect, the invention provides a method for producing a helper-infected host cell. The method includes the step of introducing to a host cell a helper, the host cell comprising an AAV rep gene and an AAV cap gene stably integrated within the host cell's chromosomes, wherein the AAV rep and cap genes are each under the control of regulatory sequences capable of directing the expression of the rep and cap genes, and wherein the host cell expresses products of the rep and cap genes upon introduction to the host cell of the helper. The helper comprises a helper virus, a helper gene, or a helper gene product.

In another aspect, the invention provides a method for producing recombinant AAV, which includes the step of introducing to the host cell of this invention which contains the helper as described immediately above, a recombinant hybrid virus. The recombinant hybrid virus comprises a selected transgene operatively linked to regulatory sequences controlling the transgene's expression. The transgene with linked regulatory sequences is flanked by AAV sequences comprising the 5' and 3' ITRs of an AAV. The 5' ITR flanks one side of the transgene, and the 3' ITR flanks the other side. The transgene with linked regulatory sequences and with flanking AAV sequences is further flanked by at least one adenovirus cis-element. The cis elements useful in this method are the cis elements required for replication of adenovirus virions and the cis elements required for encapsidation of adenovirus virions. The method optionally includes the additional step of isolating from the hybrid-virus-infected helper-infected host cell a recombinant AAV, the recombinant AAV comprising the transgene. This method permits recombinant AAV to be produced by the cell.

In one embodiment of the aspects of this invention, a method for producing recombinant AAV is referred to as the B50/hybrid method. This method includes the steps of infecting one of the host cells described herein with a helper (e.g., virus, gene or gene product) to induce AAV rep and cap expression and provide necessary helper functions, and transfecting the infected host cell with a recombinant adenovirus-AAV hybrid virus, which carries a selected transgene. In one desirable embodiment, production of AAV occurs in a two step process: A host cell of this invention which stably expresses rep and cap (e.g, B-50) is infected with helper, e.g., an adenovirus preferably defective in E2b, followed by infection with another virus, e.g., a hybrid virus, one example of which is an AdAAV hybrid in which an AAV vector containing a transgene under the control of regulatory sequences, is cloned in the E1 region of a replication defective adenovirus. This results in a 100-fold amplification and rescue of the AAV genome, leading to high yield of recombinant AAV that is free of rcAAV.

Other aspects and advantages of the present invention are described further in the following detailed description of the preferred embodiments thereof.

DETAILED DESCRIPTION OF THE INVENTION

Figure 1:
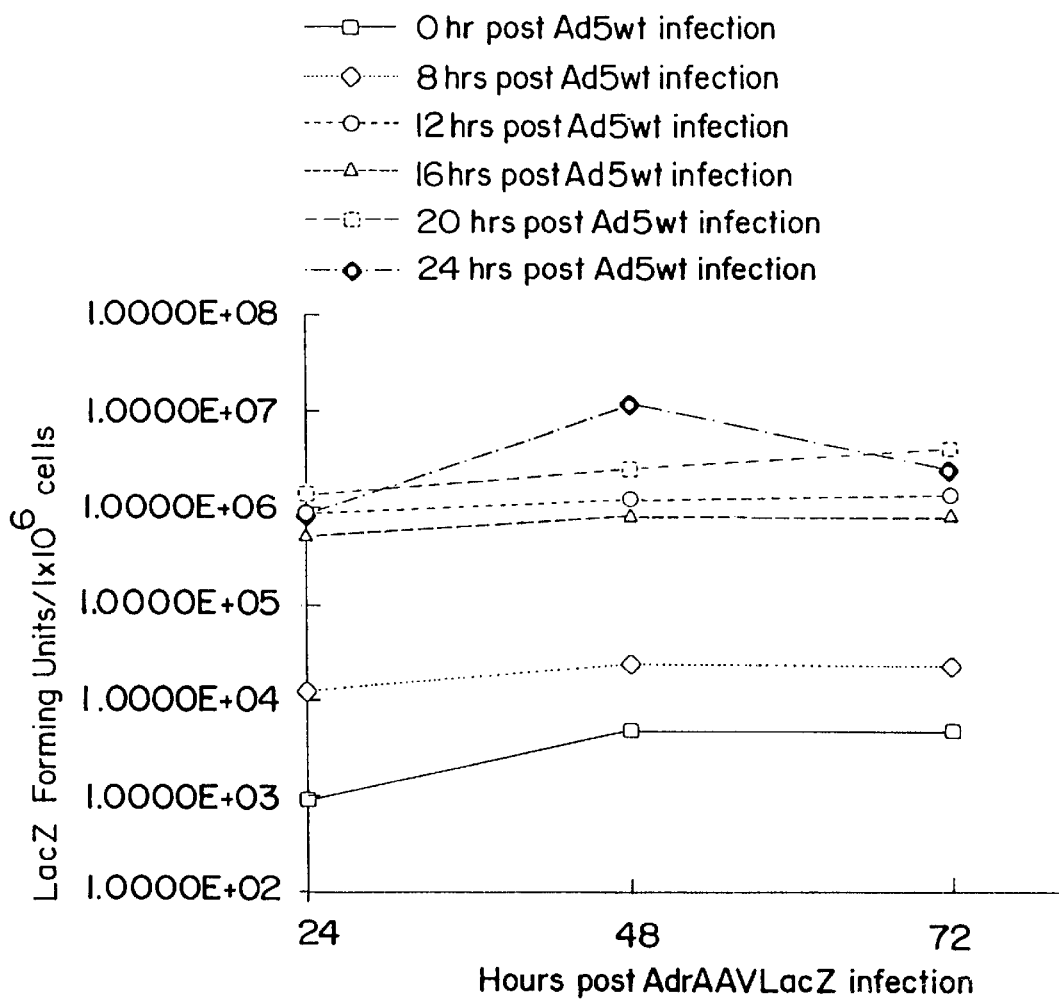
FIG. 1 is a graph illustrating the productivity of a rAAV carrying a LacZ transgene in B-50 host cells which were infected with wildtype adenovirus type 5 (Ad5wt) and transfected with a hybrid virus according to this invention. The symbols represent hours post Ad5wt infection: 0 hours (□); 8 hours (open diamond); 12 hours (○); 16 hours (Δ); 20 hours (cross-hatched square); 24 hours (cross-hatched diamond).

The invention provides methods and compositions for the production of recombinant adeno-associated virus (rAAV) in yields of greater than about $1 \times 10^3$ viral particles per cell to much higher viral particle yields, as described below. The method of this invention can be desirably employed to produce rAAV carrying transgenes, which correct a defect in a cell to modulate or alleviate the symptoms associated with the defect. These methods are particularly useful in transferring the transgene to a host cell or tissue. These rAAV are useful as research reagents, as tools for the recombinant production of a transgene product in vitro, and as tools for the production of gene therapy reagents.

I. Definitions

Recombinant AAV (rAAV) as used herein, is defined as a structure containing an AAV capsid, necessary AAV cis elements, and a heterologous gene (i.e., a transgene) of interest which is under the control of regulatory sequences (e.g., a promoter and/or regulator sequence) which direct the expression of the product of the gene under suitable conditions. Suitably the AAV cis elements include the AAV 5' and 3' inverted terminal repeats sequences (ITRs). The rAAV is devoid of the rep gene and other AAV structural genes. The rAAV is not itself capable of replication. The term rAAV encompasses functional modifications to the AAV cis elements Replication competent AAV (rcAAV) is defined herein as any AAV which can replicate in the presence of a helper which can transactivate the AAV rep and cap genes, e.g., an adenovirus helper. rcAAV must contain rep and cap. Thus, examples of rcAAV include wildtype (wt) AAV, modified wtAAV resulting from, e.g., unwanted homologous recombination, or a rearranged AAV containing a portion of a transgene resulting from, e.g., unwanted homologous recombination, so as to accommodate the rep and cap genes.

The terms "genome copies" and "particle number" are interchangeable, and are measurements of productivity (or yield) of a packaging cell line of this invention. These terms refer to the average number of rAAV virus particles that can be produced per host cell or production/packaging cell line, and is correlated to infectious units. The genome copy or particle number is a measurement of AAV DNA only, without regard to whether the AAV particle is infectious. The yield (i.e., the genome copy) is not influenced by concentration or purification. For evaluation of a cell line, the higher the genome copy or particle number, the more productive the cell. Cells of the present invention are characterized by genome copies greater than $1 \times 10^3$. Other cells of this invention are characterized by genome copies greater than $5 \times 10^3$. Still other cells of the present invention are characterized by genome copies greater than $1 \times 10^4$. Other cells of this invention are characterized by genome copies greater than $5 \times 10^4$. Cells of the present invention are characterized by genome copies greater than $1 \times 10^5$. Other cells of this invention are characterized by genome copies greater than $5 \times 10^5$. Still other cells of the present invention are characterized by genome copies greater than $1 \times 10^6$. Wherever in the following description, a cell of this invention is characterized by the phrase "high yield" or "efficient production", such phrases are defined numerically by the genome copy numbers above.

Infectious Unit (IU) or Infection Forming Unit (IFU), as used specifically herein, provides a measurement of the ability of an rAAV particle to infect a cell. One IU is equivalent to one LacZ forming unit (LFU), which is a term applied only to the rAAV harboring the transgene beta-galactosidase. IU can be measured either with or without the purification process which separates adenovirus or other helper virus from the rAAV. IU can be affected by purification or concentration. The smaller the IU, the more infectious is the AAV particle. As used in this specification, one IU or one LFU is equivalent to less than about $1 \times 10^6$ viral particles. In other embodiments of this invention, one IU is equivalent to less than $1 \times 10^5$ viral particles. More desirably, one IU is equivalent to less than $1 \times 10^4$ particle numbers. Preferably one IU is equivalent to less than $1 \times 10^3$ particle numbers.

The term "genome titer" generally refers to the genome copy or particle number per milliliter.

The term "transducing unit" or "transduction unit" is defined herein as the number of cells transduced with infectious rAAV. This term is also referred to as the potency of rAAV. Each infected cell may contain greater than one infectious AAV particle.

II. Host Cells of the Invention

A cell or host cell of the present invention is a cell, preferably a mammalian cell, that comprises an AAV rep gene and an AAV cap gene stably integrated within the cell's chromosomes. The host cell itself is preferably a mammalian cell, of which many suitable types are well-known in the art. Suitable parental cell lines which can be used to prepare host cells and host cell lines of this invention include, without limitation, HeLa [ATCC CCL2], A549 [ATCC Accession No. CCL 185], KB [CCL 17], Detroit [e.g., Detroit 510, CCL 72] and WI-38 [CCL 75] cells. These cell lines are all available from the American Type Culture Collection, 10801 University Boulevard, Manassas, Va. 20110–2209 USA.

The AAV rep and cap genes in the host cell may be obtained from among the many known serotypes of AAV. Both genes may be derived from the same AAV serotype or from different AAV serotypes. The rep and cap genes in the host cell of the invention are operatively linked to regulatory sequences capable of directing the expression of the rep and cap genes. The rep gene may be operatively linked to a different regulatory sequence than that directing the expression of the cap gene. Alternatively, the rep and cap genes may be operatively linked to the same regulatory sequences in the host cells. Such regulatory sequences are conventional and include promoters and other sequences which control translation and expression of the gene products. These regulatory sequences may be exogenous to the host cell.

The regulatory sequences may include constitutive promoters or regulated (inducible) promoters, which will enable controlled expression of the rep/cap. For example, one promoter is the liver specific albumin promoter. Another desirable promoter is a β-actin promoter, which is desirably used in combination with a cytomegalovirus (CMV) enhancer. Still other non-AAV promoters include, without limitation, the Rous sarcoma virus LTR promoter/enhancer, the cytomegalovirus immediate early promoter/enhancer [see, e.g., Boshart et al, Cell, 41:521–530 (1985)], and the inducible mouse metallothienien promoter. Still other promoter/enhancer sequences may be selected by one of skill in the art.

However, in a preferred embodiment, the regulatory sequences include AAV regulatory sequences, such as the AAV p5 promoter. The AAV regulatory sequences, e.g., the p5 promoter, may be derived from a different AAV serotype than that which provided the rep and cap genes. Alternatively, the same AAV serotype may provide all of the AAV components of the host cell.

The cells of the present invention are also characterized by the presence of the rep and cap genes in multiple copies stably integrated within the cell's chromosomes. These multiple copies may be present in the chromosomes in concatameric form, i.e., head-to-tail or head-to head order. Thus, cells of the present invention are characterized by the presence of the rep and cap genes in at least two copies stably integrated within the cell's chromosomes. Other cells of the present invention are characterized by the presence of the rep and cap genes in at least three copies stably integrated within the cell's chromosomes. Still other cells of the present invention are characterized by the presence of the rep and cap genes in at least four copies stably integrated within the cell's chromosomes. An embodiment of a cell of this invention described below contains five copies of rep/cap stably integrated with the cell's chromosomes. These multiple copies may also contain repeated copies of the promoter/regulatory sequences which control expression of the rep/cap.

The cells of this invention express the gene products of the rep and cap genes upon introduction to the cell of a helper. Appropriate helpers are identified in the description of the methods below.

When appropriate helpers and hybrid viruses are introduced to the cells of the present invention, according to the methods described in detail in part III below, the cells of the present invention are characterized by efficient production of high yields of rAAV in contrast to the productivities of packaging cells of the prior art. When used to produce rAAV in the below-defined methods, the productivity of cells of this invention may be defined as producing yields of rAAV greater than $1 \times 10^3$ genome copies per cell. Cells of this invention are also characterized by producing at least $3 \times 10^3$ genome copies per cell. Other cells of this invention are characterized by yielding at least $1 \times 10^4$ genome copies per cell. Still other cells of this invention are characterized by producing greater than $5 \times 10^4$ genome copies per cell. Other cells of this invention are characterized by producing yields of greater than $1 \times 10^5$ genome copies per cell. Cells of this invention are characterized by producing greater than $5 \times 10^5$ genome copies per cell. The cells of this invention are characterized by genome copies of greater than $1 \times 10^6$ genome copies per cell.

One illustrative embodiment of a host cell of this invention is B-50. This B-50 cell line was deposited with the American Type Culture Collection, 10801 University Boulevard, Manassas, Va., United States of America 20110–2209, USA 20852 on Sep. 18, 1997 under Accession number CRL 12401 pursuant to the requirements of The Budapest Treaty on the International Recognition of the Deposit of Microorganisms for the Purposes of Patent Procedure. B-50 is a HeLa cell line, which, upon the introduction of a helper, stably expresses AAV type 2 rep and cap genes under the control of the homologous p5 promoter. B-50 is characterized by integration of multiple copies (at least 5 copies) of P5-rep-cap gene cassettes in a concatamer form into the host chromosome. B-50 demonstrates stable, efficient and high yield expression of rep and cap upon adenovirus infection. B-50 is an improvement over other stable rep/cap expressing cell lines, such as those described in U.S. Pat. No. 5,658,785, because of its unusually and unexpectedly high level of expression of the rep and cap gene products. The expression level and protein profile of rep/cap in B-50 cells infected with adenovirus helper are between 5-fold to 10-fold better than those attributes of HEK293 cells transfected with pAd/AAV, a plasmid construct containing the entire AAV coding sequences including p5 promoter [Samulski, R. J. et al, *J. Virol.*, 63:3822–3828 (1989)] and being widely used for rAAV production by classical transfection methods.

The host cells of this invention, including e.g., B-50 cells, can be used not only for large scale production of rAAV through the methods of this invention described in detail below, but also for generating rAAV producer cell lines with a gene of interest. In addition, the cells of this invention have many other applications such as titering rAAV preparation in assays, e.g., an Infectious Center Assay [Snyder, R. O. et al, "Production of recombinant adeno-associated viral vectors.", in *Current Protocols in Human Genetics*, Vol. 1, (eds. Dracopoli, N. et al.) pp 1–24 (John Wiley & Sons, N.Y. 1996)] and as research tools for studying the biological functions of rep/cap proteins, promoter influence, cell cycle regulation, and the like.

III. Method of the Invention

The present invention also provides methods for producing a helper-infected host cell and methods for producing the aforementioned high yields of rAAV by using the infected host cells of the invention. These methods of the present invention provide a response to the need for gene delivery vectors which may be efficiently produced in high yields and which are substantially purified. The methods of the present invention do not require transient transfection, but instead utilize introduction to the cell line of the present invention a helper.

According to these methods, a helper is introduced to a host cell as described above, i.e., a mammalian cell comprising an AAV rep gene and an AAV cap gene stably integrated within the host cell's chromosomes, wherein the rep and cap genes are each under the control of regulatory sequences capable of directing the expression of the rep and cap genes. In the presence of the helper, the host cell expresses the gene products of the rep and cap genes.

The helper may be in the form of a helper virus, or a plasmid; or it may be delivered as a helper gene, or a helper gene product or as some other construct. The helper is capable of providing helper functions (i.e., capable of activating the expression of the rep and cap genes in the host cell) in any of its forms. Use of the term "helper virus" in this application means any of these elements capable of providing helper functions. Thus, in one example, the helper includes the adenovirus E1 gene or gene product. The E1 gene may be delivered to the cell by infection with an E1-containing adenovirus, e.g., a wild-type or otherwise modified E1-containing adenovirus, or a recombinant adenovirus or a plasmid containing E1. The gene Product may be delivered directly to the cell. Alternatively, the transactivating helper may be another virus (not an adenovirus) which contains the adenovirus E1 gene and functions to deliver the AdE1 gene to the cell line. Such other virus may be selected from among a number of known viruses commonly employed to vector exogenous genes to cells.

Still another alternative transactivating helper is a herpes virus, which also has the ability to activate rep/cap expression from an AAV P5 promoter, among others. The helper may be a wildtype herpes virus, a recombinant herpes virus, a herpes virus gene, or a herpes virus gene product. The gene product may be delivered directly to the cell. Among suitable herpes viruses are Herpes simplex I and Herpes Simplex II. Also useful as transactivating helper viruses are Vaccinia and Cytomegalovirus. These viruses may be modified or replication defective.

Alternatively, the helper virus may be a temperature sensitive mutant virus which will be self-replication defective at non-permissive temperatures, and therefore, will only provide necessary helper functions to rAAV production.

As reported in the prior art, those adenovirus genes necessary for maximal AAV production levels appear to include E1, E2a, E4 and VAI [Kotin, R. M. *Hum. Gene Thera.* 5, 793–801 (1994)]. Such other helper genes which are necessary for rAAV production may be introduced to the cell in the same manner as E1, described above, i.e., in the same helper construct or virus. Alternatively, helper genes other than the transactivating helper, e.g., E1, may be delivered at some time after the transactivating helper by introducing an additional helper to the cell. For example, the helper genes other than E1 may be delivered to the host cell via a replication-defective adenovirus, among other helpers.

Once the helper, or at least the transactivating helper is introduced to the cell, it may employed in a method for producing recombinant AAV. The method of this invention is based on infecting the helper-containing, rep/cap expressing cell line of the invention with recombinant hybrid virus, e.g., an Ad-AAV hybrid virus, which substantially increases the yield of rAAV and simplifies scale-up, allowing the study of multiple subjects from a single preparation of rAAV.

The recombinant hybrid virus comprises a selected transgene operatively linked to regulatory sequences controlling the transgene's expression, the transgene with linked regulatory sequences being flanked by AAV sequences comprising the 5' and 3' ITRs of an AAV, wherein the 5' ITR flanks one side of the transgene, and the 3' ITR flanks the other side. The transgene with linked regulatory sequences and with flanking AAV sequences is flanked by at least one adenovirus cis-element. The cis-element is selected from among cis elements required for replication of adenovirus virions and cis elements required for encapsidation of adenovirus virions.

One embodiment of a hybrid AdAAV virus which can be used in the methods of this invention is described in detail in International Patent Publication No. WO96/13598, published on May 9, 1996, and incorporated by reference herein. Essentially, the AdAAV hybrid virus or a hybrid virus vector (plasmid) as described above provides in cis a minigene, which comprises a selected heterologous transgene under the control of regulatory sequences directing expression thereof in the host cell. The introduction of the hybrid virus or vector into the host cell is accomplished using known techniques. The use of the hybrid virus, which substantially amplifies the AAV DNA prior to rescue and replication, is believed to assist in generating high yields of rAAV produced by the methods of this invention.

The introduction of a helper which can transactivate (e.g., activate the promoter controlling expression of rep/cap in the cell) the rep/cap expression in the stable rep/cap expressing cell line of this invention and provide helper functions for AAV replication, followed by the introduction of the Ad-AAV hybrid virus provides the components necessary for rAAV production.

Recombinant AAV comprising the transgene are produced by the cell and are isolated therefrom in high yields as identified above (e.g., the recombinant AAV is produced at levels exceeding $1 \times 10^3$ genome copies per cell). Also, e.g., the rAAV may also be produced at a level exceeding $1 \times 10^6$ genome copies per cell. These recombinant AAV are essentially homogenous, that is, the rAAV produced by the method of this invention are essentially free of replication-competent AAV. See the embodiment discussed in Example 4 below.

In the methods described herein, the temporal relationship between rep/cap induction and AAV rescue and replication as well as infectious dose, i.e., the multiplicity of infection (MOI) of the helper and AdAAV hybrid viruses, can be readily adjusted to optimize rAAV production, depending on the cell line, helper(s) and AdAAV hybrid used. Such adjustments are accomplished by performing experiments varying the times of helper introduction(s), hybrid virus infection and MOIs of helper(s) and hybrid. See, e.g., the experiments described above and reported in FIG. 2A and 2B and in the examples below. For example, in the embodiments described in FIG. 2A, for example, the time between infection of the wild type and hybrid viruses was varied, demonstrating a substantial increase in rAAV production with maximal yields obtained when a cell of this invention was infected with hybrid virus between 12 to 36 hours after the helper was introduced to the cells. In that particular embodiment of FIG. 2A, the introduction of hybrid virus 24 hours after the introduction of helper was optimal. Balancing dosage and temporal aspects of these methods are routine protocols and may be performed to determine the best conditions for the parameters of the method. Such protocols as described in the Examples below are skills well within the art.

In one particular embodiment of a method of this invention referred to as the B-50/hybrid method, the B-50 cell line, which is capable of stable expression of rep/cap from an endogenous AAV promoter, is sequentially infected with a helper virus, preferably an E1-expressing, E2b defective adenovirus, to activate rep/cap and provide helper function, and an Ad-AAV hybrid virus, which efficiently transfers and replicates the AAV vector sequence. Preferably, the helper adenovirus expresses the adenovirus E1 gene product. The helper-infected host cell is then infected with a recombinant AdAAV hybrid virus, which comprises (1) adenovirus cis-elements necessary for replication and virion encapsidation; (2) AAV sequences comprising the 5' and 3' ITRs of an AAV, these AAV sequences flanked by the adenovirus sequences of (1); and (3) a selected gene operatively linked to regulatory sequences directing its expression, said gene and regulatory sequences flanked by the AAV sequences of (2). Preferably the sequence and timing of AAV rep/cap induction by the action of the helper virus relative to vector replication is balanced by infecting the cell line with the helper virus prior to infection with the hybrid virus. In one scaled-up embodiment, the infections are performed in bioreactors containing B50 cells adapted for growth in suspension. Following infection with a helper virus and transfection with the hybrid virus or vector, the host cell is then cultured under standard conditions, such as described in e.g., F. L. Graham and L. Prevec, *Methods Mol. Biol.*, 7:109–128 (1991). Desirably, once the rAAV is identified by conventional means, it may be recovered and purified.

Important aspects of rAAV production for in vivo applications according to this method are purification and characterization of the product. Potential contaminants include rcAAV, cellular DNA, the helper(s) and/or hybrid virus. The methods of this invention avoid the most troublesome contaminate, i.e., rcAAV. Contaminating cellular DNA is minimized by pretreatment of the vector with DNase. Elimination of adenovirus is preferably accomplished by a combination of steps. Heat denaturation with sedimentation through cesium effectively eliminates functional adenovirus (<1 pfu Ad/$10^{11}$ rAAV genomes) and substantially diminishes contaminating adenovirus genomes (<0.00004% of total DNA) when used in the method of this invention. Methods more amenable to large scale production, such as column chromatography, are also useful.

As described in the examples below, the biological potency of AAV prepared by this method was evaluated in mice using erythropoietin (Epo) as an easily detected and quantified secreted protein, and beta-galactosidase (lacZ), as an easily detected histochemical marker. Recombinant AAV produced by an embodiment of a method of this invention performed better (i.e., were more infectious) than rAAV made by conventional procedures of 293/cotransfection, when tested in mice. Furthermore, transgene expression from the rAAV produced by the present methods increased in proportion to vector dose. See, e.g., Example 5 below.

The following examples illustrate several preferred methods of the invention. While the examples below employ the B50 cell line and a wildtype adenovirus as helper, those of ordinary skill in the art will understand that any cell having the elements described above may be substituted for the B50 cell line, and any helper fulfilling the above-described helper functions (i.e., activating rep/cap expression) may be substituted for the wildtype adenovirus. These examples are thus illustrative only and are not intended to limit the scope of the invention.

EXAMPLE 1

Construction and Characterization of the B-50 Rep/Cap Complementing Cell Line

The inventors stably transfected into a number of cell lines, rep/cap containing plasmids in which rep and cap are expressed from an inducible promoter. These included the endogenous P5 promoter of AAV induced by E1a of adenovirus as well as the heterologous promoters from the mouse metallothienien gene induced by divalent cations, and the long terminal repeat of murine mammary tumor virus induced by glucocorticoids. To overcome the problems associated with conventional rAAV production methods involving transfection of cis and trans plasmids in combination with helper adenovirus infection, three plasmid vectors were constructed for generating rep/cap cell lines.

Each plasmid vector contained a neomycin selective marker gene and expressed the AAV rep/cap genes driven by either their native P5 promoter (pP5-Rep/Cap), or the zinc-inducible sheep metallothionine promoter (pMTRep/Cap), or the dexamethasone (Dex)-inducible mouse mammary tumor virus (MMTV) promoter (pMMTV-Rep/Cap). These rep/cap expressing plasmids were derived from previously published constructs used to create an Ad E4-orf6 cell line in which the P5 rep/cap fragment of pSub20l was replaced with orf6. Specifically, for construction of pMT-Rep/Cap, ORF6 sequence was removed from pMTE4ORF6 plasmid [G. P. Gao et al, *J. Virol.*, 70:8934–8943 (1996)] by BamHI digestion and replaced with a 4.1 kb rep/cap fragment which was prepared by PCR amplification using the pSub201 plasmid [Samulski, R. J. et al., *J. Virol.*, 63:3822–3828 (1989)] as a template. pMMTV-Rep/Cap was constructed in the same way as pMT-Rep/Cap, except that the pMMTVE4ORF6 plasmid was used as the vector backbone. For construction of P5-Rep/Cap, the MT promoter and ORF6 sequences were removed from the pMTE4ORF6 plasmid by EcoRI/BamHI digestion and replaced with a 4.3 kb P5-Rep/Cap fragment which was isolated from the pSub201 plasmid by XbaI digestion. Plasmid construction involved conventional genetic engineering methods, such as those described in Sambrook et al, cited above.

First, the functionalities of these constructs were confirmed by transient transfection into 10-3-rAAVLacZ cells, a 293-based cell line containing integrated forms of AdE4ORF6 and rAAVLacZ genes [James M. Wilson's laboratory, The University of Pennsylvania] in the presence or absence of wildtype adenovirus type 5 and appropriate inducers, i.e., 150 $\mu$M $ZnSO_4$ for pMT-Rep/Cap, and 10 $\mu$M dexamethasone for pMMTV-Rep/Cap. Transfection of all three constructs into 10-3-rAAVLacZ cells led to rescue of rAAVLacZ from the cells. This demonstrated that all three constructs produced functional rep/cap proteins.

Second, all three constructs were stably transfected into both HeLa and A549 cells, which are available commercially from the American Type Culture Collection. Stable transfectant colonies were selected in the presence of culture media containing the antibiotic G418 (Geneticin) for two weeks, and were expanded individually.

These clones were evaluated for the capacity to transcomplement in the production of rAAVLacZ by transiently transfecting the cells with prAAVLacZ, a cis plasmid for producing rAAV LacZ which contains an CMV-$\beta$-galactosidase-SV40 poly A minigene cassette flanked by AAV ITRs [Fisher K. J. et al, *J. Virol.*, 70:520–532 (1996)], via DOTAP in the presence of Ad5Wt and appropriate inducers. For clones transfected with pMT-Rep/Cap, 150 $\mu$M $ZnSO_4$ was added to the culture medium 24 hours prior to adenovirus infection at MOI of 5. For clones transfected with pMMTV-Rep/Cap, 10 $\mu$M dexamethasone was added to the culture medium 24 hours prior to adenovirus infection at an MOI of 5. Infection with Ad5 induced expression from the P5 promoter. Seventy-two hours post-transfection/infection, the infected clones were harvested when full CPE was demonstrated. The viral lysate of each clone was made by three rounds of freezing and thawing. One-tenth of each viral lysate was heat-incubated at 56° C. for 30 minutes and used to infect 84-31 cells, an E1/E4-double complementing cell line [Gao et al, cited above]. Twenty-four hours post infection, the cells were stained with 5-bromo-4-chloro-3-indolyl-$\beta$-D-galactopyranoside (X-gal) for $\beta$-galactosidase expression [see e.g., J. Price et al, *Proc. Natl. Acad. Sci. USA.*, 84:156–168 (1987)] and the percentage of blue cells was scored. Clones scoring as positive were subject to a number of additional studies including DNA hybridization, immunocytochemistry, and Western analysis for E1a, rep, and cap after infection with wild type Ad5.

The results are summarized as follows: 708 total $G418^R$ colonies were picked. From these, 618 clones were subcultured. 515 of the 618 clones survived expansion and screening. From the screen, only 8 positive clones were able to transcomplement rep/cap. One of these eight clones, designated B-50 (created by transfecting the P5-rep/cap plasmid into HeLa cells) was found to express rep and cap gene products at high levels. These 8 clones were further characterized for their genetic constitution, rep/cap protein expression upon induction, and rAAV production.

B-50 was the only clone in which the rep/cap gene sequence was detected by Southern blotting of genomic DNAs from the cell lines digested with BamHI. The copy numbers of rep/cap genes and the forms of the genes (episome v.s. integrated) in the cell were confirmed by repeating the Southern Blot with both total genomic and Hirt's DNA prepared from B-50 cells. DNA hybridization analysis revealed five copies of the plasmid arranged in a head-to-tail concatamer (data not shown). In B-50 cells, the rep/cap genes are stably integrated into the genome and there is no episomal form of rep/cap sequences detectable by Southern blot.

In addition, high levels of rep/cap protein expression was detected in B-50 by Western blotting (i.e., yielding 100-fold more vector than the others). Double immunofluorescent staining of adenovirus infected B-50 cells for the AdE1b early protein or late proteins and rep/cap proteins demonstrated that B-50 is a homogenous cell line. The stability of the B-50 cell line was demonstrated by its rAAV productivity, comparing passage 5 to passage 15.

EXAMPLE 2

The Kinetics of Rep/Cap Induction in B50 Cells

The kinetics of rep/cap induction in B50 cells was determined following infection with adenovirus. B50 cells were infected with wild type Ad5 at an MOI of 10 and total cellular proteins were prepared at different time points post-infection. Samples (50 $\mu$g) were fractionated on 10% SDS-PAGE gels and electrotransferred into nitrocellular membranes. Rep and cap proteins were detected with ECL system (Amersham Life Science) using mouse monoclonal antibodies clones 259.5 and B1 (American Research Products, Inc.) respectively. Adenovirus E1 protein was detected by a mouse monoclonal antibody against Ad2 E1a (Oncogene Science). The expression of E1a, rep protein, and cap proteins were observed on the gel (data not shown) as a function of time after infection and are summarized below.

In the absence of adenovirus, rep/cap proteins are not expressed. Infection with adenovirus results in a temporally regulated program of gene expression with E1a protein peaking at 20–24 hours, followed by the induction of substantial quantities of all rep and cap proteins, which reach maximal levels by 44 hours and are sustained until the cells reach full cytopathology by 62 hours. Levels of rep/cap expression are equivalent to that observed following a wild type of AAV infection, although profiles are different in that proportionally greater rep 52/40 are expressed relative to rep 78/68 and more VP3 is expressed relative to VP1 and VP2, as compared to the profile of a wildtype infection.

EXAMPLE 3

Recombinant AAV Production in the B-50 Cell Line

The productivity of rAAV expression by B-50 was assessed by infecting the cells at different MOIs with either (a) recombinant hybrid AdAAV virus and wildtype adenovirus type 5 (Ad5Wt) simultaneously; or (b) Ad5Wt alone for 8, 12, 16, 20 and 24 hours prior to infection with the hybrid AdAAV virus A. Hybrid Virus Construction The procedure for constructing hybrid AdAAV vectors has been described [Fisher et al, *Hum. Gene Ther.* 7:2079–2087 (1996)]. Briefly, rAAV genome containing a minigene cassette with the gene of interest and flanking AAV ITRs was isolated by PvuII restriction endonuclease digestion from prAAV cis plasmid and cloned into the EcoRV site of the shuttle plasmid pAdBglII. Transgenes included green fluorescent protein (GFP), LacZ, and a cDNA encoding erythropoietin from rhesus monkeys isolated by RT-PCR of RNA from pituitary. Each vector expressed the transgene from the immediate early promoter of cytomegalovirus. The resulting constructs consist of the 5' sequence of Ad (map unit 0–1), a copy of rAAV genome, and Ad sequence spanning map units 9–16.1. Adenoviral DNA was prepared for cotransfection by digestion with ClaI. The supercoiled plasmid DNA of pAdAAV was used for cotransfection using a standard calcium phosphate precipitation protocol and recombinant hybrid viruses were isolated as described in Fisher, cited above.

As one example the hybrid virus, H5.010rAAVLacZ (also Ad.AV.CMVLacZ) was created by cloning an rAAV genome in place of E1 in an Ad5 based virus. This hybrid virus is described in detail in Example 1 of International publication WO96/13598, cited above and incorporated by reference herein. It contains the 5' AAV ITR (bp 1–173) from AAV type 2, a CMV immediate early enhancer/promoter [Boshart et al, *Cell*, 41:521–530 (1985), an SV40 intron, *E. coli* beta-galactosidase cDNA, an SV40 polyadenylation signal and 3' AAV ITR from AAV2, flanked by adenovirus type 5 map units 0–1 on one side and substantially all of m.u. 9–100 on the other.

B. Experimental Protocol

B50 cells were seeded in 60 mm² plates at a density of $2 \times 10^5$ cells per plate overnight. The cells were infected with wild type Ad5 and hybrid Ad.AV.CMVLacZ simultaneously. Alternatively, the cells were infected with wild type Ad5 at 8, 12, 16, 20 and 24 hours prior to infection with hybrid Ad.AV.CMVLacZ at an MOI of 10.

Total cellular lysates were prepared at 48 hours post hybrid Ad.AV.CMVLacZ infection by 3 rounds of freezing/thawing and heat-inactivation at 56° C. for 1 hour. Production of rAAVLacZ in each sample was determined by infecting 84-31 cells, an E1/E4-double complementing cell line permissive for rAAV transduction, with the cellular lysate in serial dilutions for 20 hours. Twenty-four hours post infection, the cells were histochernically stained with X-gal and LacZ Forming Units (LFUs), i.e., blue cells, were counted.

Figure 2A:
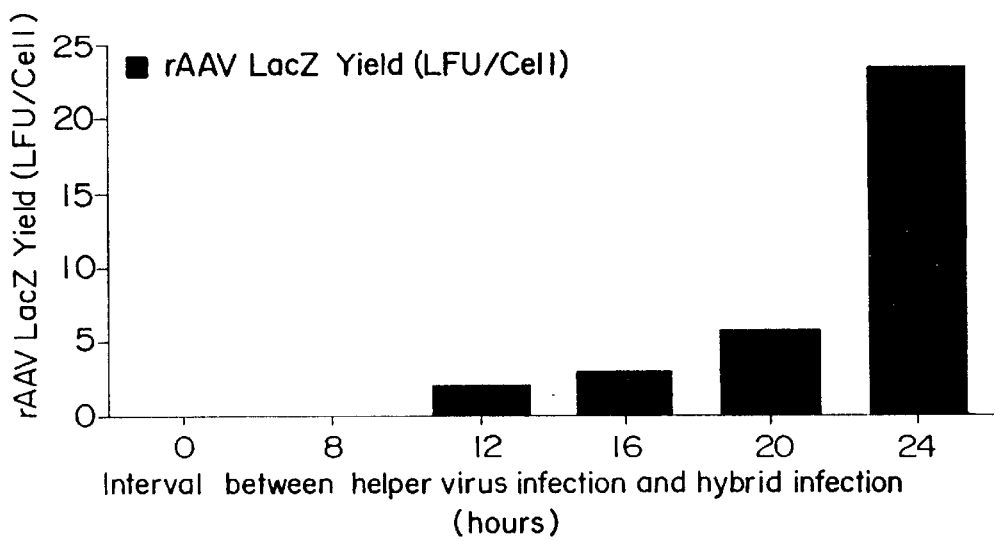
FIG. 2A is a bar graph demonstrating amplification of AAV genome in the hybrid shuttle virus Ad.AVCMVLacZ (also Ad-AAVlacZ) and the impact of infection sequence on vector production in B50 cells, as reported in Example 2. The production of rAAV under different conditions is represented infectious units referred to as lacZ forming units (LFU) per cell vs. time interval between infection by the helper virus and infection with the hybrid virus.

The production of rAAV under different conditions is shown in FIG. 2A, with the rAAV represented as lacZ Forming Units per cell on Y axis vs. interval between helper and hybrid infection. These experiments were repeated on two occasions with identical results.

C. Experimental Protocol

In another experiment, the B50 cells were seeded as described above and infected with wild type Ad5 24 hours prior to Ad.AV.CMVLacZ at an MOI of 10. Total cellular lysates were prepared at 2 to 72 hours post the hybrid virus infection by 3 rounds of freezing/thawing. Duplicates of each sample were either treated at 56° C. for 1 hour or not treated and assayed for LFU as above.

Figure 2B:
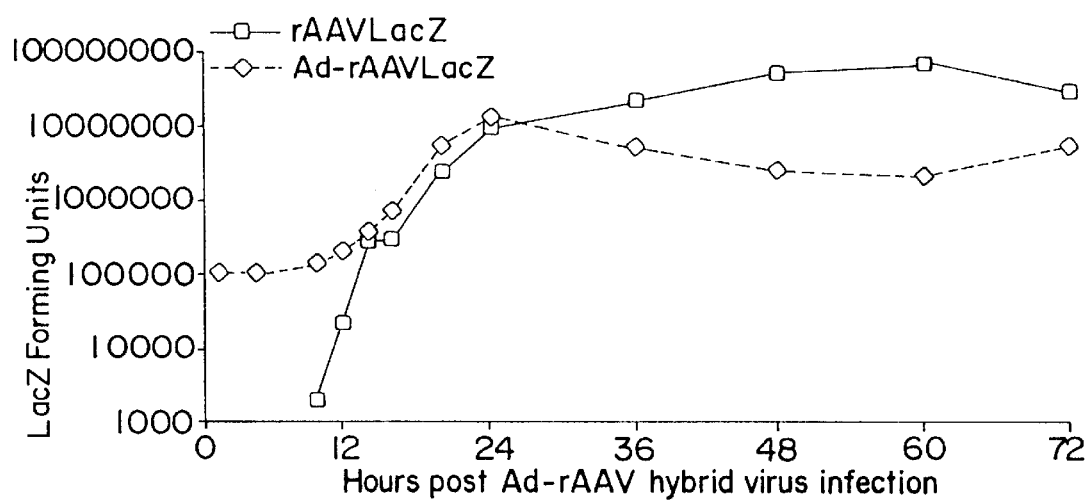
FIG. 2B is a graph showing amplifications of hybrid virus and rAAV in B50 cells which were infected with Ad5wt 24 hours prior to Ad-AAVlacZ at a multiplicity of infection (MOI) of 10. See the detailed protocol of Example 2. The dotted line represents growth kinetics of the hybrid which is defined as the transduction measured after heat inactivation. The solid line indicates excision and amplification of rAAV genomes and production of vector as measured by transduction after heat inactivation.

The results are reported in FIG. 2B. The dotted line represents growth kinetics of the hybrid which is defined as the transduction measured after heat inactivation. The solid line indicates excision and amplification of rAAV genomes and production of vector as measured by transduction after heat inactivation.

D. Experimental Protocol

In another experiment, B-50 cells were infected at 0, 8, 12, 16, 20, and 24 hours post Ad5wt infection (MOI of 20) with rAd.AV.CMVLacZ. Cell lysates were prepared at 24, 48 and 72 hours post infection by the hybrid AdAAV vector described in Example 2 for LFU assays on 84-31 cells.

The data was reported in FIG. 1, and shows that where B-50 cells were pre-infected at an MOI of 20 with Ad5wt for 24 hours, and then infected with rAdAAV for 48 hours, B-50 cells can produce at least 10 LFU of rAAVLacZ per cell.

E. Experimental Protocol

In still another experiment, B-50 cells in 60 mm plates (about $1.5 \times 10^6$ cells per plate) were infected with Ad5wt at MOI of 1, 2, 5, and 10 for 24 hours and then superinfected with H5.010rAAVLacZ at the corresponding MOIs. The cells were harvested at 18, 24, 36, 48 and 60 hours post H5.010rAAVLacZ infection and the lysates were used to determine LFU on 84-31 cells. The results of such an LFU assay are shown below in Table 1. The figures reported in column 3 are the total LFU obtained from samples containing $1.5 \times 10^6$ cells.

TABLE 1

| MOI | Hours post hybrid infection | Total LFU | LFU/cell |
|---|---|---|---|
| 1 | 18 | $1.6 \times 10^5$ | 0.1 |
| 1 | 24 | $2.0 \times 10^6$ | 1.4 |
| 1 | 36 | $1.3 \times 10^7$ | 8.8 |
| 1 | 48 | $1.8 \times 10^7$ | 12 |
| 1 | 60 | $1.7 \times 10^7$ | 11.5 |
| 2 | 18 | $8.0 \times 10^4$ | 0.05 |
| 2 | 24 | $9.8 \times 10^6$ | 6.5 |
| 2 | 36 | $1.9 \times 10^7$ | 12.3 |
| 2 | 48 | $3.1 \times 10^7$ | 21 |
| 2 | 60 | $2.0 \times 10^7$ | 13.5 |
| 5 | 18 | $1.4 \times 10^6$ | 1.0 |
| 5 | 24 | $2.1 \times 10^7$ | 14 |
| 5 | 36 | $4.7 \times 10^7$ | 32 |
| 5 | 48 | $3.5 \times 10^7$ | 23 |
| 5 | 60 | $2.8 \times 10^7$ | 19 |
| 10 | 18 | $1.2 \times 10^6$ | 0.8 |
| 10 | 24 | $2.0 \times 10^7$ | 13 |
| 10 | 36 | $5.2 \times 10^7$ | 35 |
| 10 | 48 | $2.7 \times 10^7$ | 18 |
| 10 | 60 | $2.8 \times 10^7$ | 19 |

F. Experimental Protocol

The method of rAAV production of the present invention was scaled-up to ~$10^9$ cells ($100 \times 15$ cm² plates) using B-50 as the cell line and Ad5wt as the helper. This method was compared to the performance of the standard method of rAAV production which is based on transient cotransfection of vector and rep/cap plasmid into 293 cells together with adenovirus infection (called 293/cotransfection method) [See, Fisher (1996) cited above]. This large scale production of AAV expressing green fluorescent protein (GFP) or rhesus monkey erythropoietin (rhEpo) was also attempted with the method of this invention, using B-50 as the cell line and the E2b defective adenovirus sub100r [provided by Jerome Schaack, UCHSC; Schaack, J. et al, *J. Virol.* 69:4079–4085 (1995)]] as the helper. These results were compared with the standard 293/cotransfection method using the same hybrid AAV plasmids and a replication defective beta galactosidase expressing recombinant adenovirus (ΔE1lacZ) as helper.

Table 2 summarizes the results of rAAV expressing GFP (AAVCMVGFP) under the control of the CMV promoter and rAAV expressing rhepo under the control of the CMV promoter (AAVCMVrhEpo). Purified preparations were analyzed for rAAV genomes and transduction. Table 2 reports a comparison of rAAV production, in which the total yield of rAAV is presented based on the production of $10^9$ cell (i.e., 100×15 cm$^2$ plates). Total transduction units (i.e., the number of infected cells) in column 3 are reported as determined by in situ analysis of reporter gene expression following limiting dilution. Total genome copies in column 4 (i.e., number of virus particles/$10^9$ cells) are determined by DNA hybridization. The abbreviation Tu/GC in column 5 represents transduction units/genome copies of average values.

standard 293/cotransfection method for other AdAAV hybrid vectors tested, which vectors contained the same AAVCMV backbone, but different transgenes, such as growth hormone and ornithine transcarbamylase, among others (data not shown).

A number of replication defective, E1 expressing adenoviruses were evaluated as potential substitutes for the wild type Ad5 helper in the production of AAV-GFP from the hybrid vector (data not shown). As expected, production of rAAV was substantially diminished with helper viruses defective in E2a or E4, both of which are necessary for AAV replication [Kotin, R. M. *Hum. Gene Thera.* 5, 793–801 (1994)]. However, temperature sensitive mutations in the E2b gene [i.e., ts 149 [Myers, M. W. et a, *J. Virol.* 35, 65–75 (1980)] and sub100r did not diminish the yield of rAAV. As reported in the prior art, those adenovirus genes necessary for maximal AAV production levels appear to include E1, E2a, E4 and VAI.

G. Experimental Protocol

Additional experiments relating to the production method of the present invention demonstrated high levels of rAAV, which exceed those obtained using the standard 293/cotransfection method with the wild type AAV as helper in control experiments. Such high yields as described above span from over 2 fold to over 20 fold the yields of the controls (e.g., a genome copy of greater than $1×10^3$ virus particles per cell through greater than $1×10^6$ particles/cell, see above). Cells of this invention, i.e., B-50 cells were

TABLE 2

| rAAV | Helper | Total Transduction Units | Genome Copies | Tu/GC | No. of Preps. |
|---|---|---|---|---|---|
| Method of the Invention | | | | | |
| AAVCMVGFP | Ad5Wt | $1.9 × 10^{10}$ | $2.2 × 10^{13}$ | 685 | 2 |
|  |  | $5.2 × 10_{10}$ | $2.5 × 10^{13}$ |  |  |
| AAVCMVGFP | Sub100r | $7.8 ± 0.8 × 10^{10}$ | $5.9 ± 0.6 × 10^{14}$ | 7564 | 3 |
| AAVCMVrhEpo | Sub100r | N/A | $7 × 10^{13}$ | N/A | 1 |
|  |  |  | $3.4 × 10^{13}$ |  |  |
| Standard 293/cotransfection method | | | | | |
| AAVCMVGFP | ΔE1lacZ | $3.3 ± 3.4 × 10^8$ | $6.4 ± 0.4 × 10^{12}$ | 19393 | 4 |
| AAVCMVrhEpo | ΔE1lacZ | N/A | $9.3 ± 7.4 × 10^{14}$ | N/A | 3 |

The standard method yielded 3.3×10$^8$ transducing units and 6.4×10$^{12}$ genome copies per 10$^9$ cells for the rAAV containing GFP, which is consistent with published results [Fisher (1996), cited above]. The method of the present invention yielded 100-fold more rAAV containing GFP, based on the transduction titers, with a 28-fold improvement in potency or number of cells transduced with infectious rAAV, as measured by a reduction in the ratio of genome copies to transduction units. Yields of GFP vector were increased with sub100r over what was obtained with wild type Ad (transducing units increased 2-fold and genome copies increased 25-fold), although potency, as measured by the ratio of vector genomes to transduction units, was decreased 11-fold. The total yield of AAV particle numbers and number of infectious units was increased overall.

A 6-fold increase in genome copies was obtained with an AAV vector expressing rhesus monkey Epo when comparing the production method of the present invention using the sub100r Ad helper to the standard 293/transfection method. In general, the production method of the present invention has demonstrated 20- to 100-fold increases in genome titer (i.e., genome copies per ml) over that obtained with the infected with the lacZ hybrid virus (Ad.AV.CMV LacZ) 24 hours after wild type Ad helper and lysates were subsequently harvested and analyzed for production of lacZ-containing AAV versus amplification of lacZ Ad.AAV hybrid virus. Specific measurements included lacZ transduction before heat denaturation (which includes hybrid virus and rAAV) and after heat denaturation (which represents rAAV). Contribution of the hybrid virus to transduction is the difference between the two transduction titers (i.e., before and after heat denaturation).

Representative kinetics of these experiments are shown in FIG. 2B which indicate that the hybrid undergoes an exponential 100-fold amplification between about 12 and about 24 hours after seeding, which immediately precedes a second round of AAV amplification of equal proportion. The hybrid virus is amplified several orders of magnitude in B50 cells prior to or concurrent with rescue and replication of the rAAV genome.

H. Summary of Experimental Results

The introduction of a helper which can transactivate (e.g., activate the promoter controlling expression of rep/cap in the cell) the rep/cap expression in the stable rep/cap expressing cell line of this invention, e.g., B-50 cells, and provide helper functions for AAV replication, followed by the introduction of the Ad-AAV hybrid virus provides the components necessary for rAAV production. Indeed, infection of B50 with a hybrid virus that contains an AAV vector expressing GFP but without provision of the transactivating adenovirus E1 gene, did not yield detectable rAAV. Further, as demonstrated, the timing of the provision of the transactivating agent, which can be an adenovirus E1 gene (by use of E1-expressing wildtype or modified adenoviruses, or by providing the Ad E1 gene in another virus vector) or which can be by provision of other virus transactivators (e.g., herpes, CMV, vaccinia), prior to introduction of the AdAAV hybrid vector can influence the yield of rAAV.

When B-50 cells were infected with Ad5Wt and H5.010rAAVLacZ at the same time, there was no rAAVLacZ produced, presumably because the replication of H5.010rAAVLacZ in the presence of Ad5Wt overrides the production of rAAVLacZ. The rAAV genome can be rescued from H5.010rAAVLacZ-infected B-50 cells only when the cells were infected with Ad 5Wt prior to H5.010rAAV LacZ infection. When the B-50 cells were infected with Ad5Wt first, onset of rep/cap protein expression inhibited adenoviral vector replication and promoted rAAVLacZ production, which forced the balance towards rAAV production instead of H5.010rAAVLacZ replication. Rep protein expression continues until full cytopathic effect (CPE), while cap protein expression becomes detectable at 20 hours post-infection, reaches the peak at 40 hours post-infection, and then reaches a plateau. The yield of rAAVLacZ under these conditions is between about $1\times10^3$ to $5\times10^3$ virus particles per B-50 cell (i.e., 1–5 LFU).

Thus, this analysis of one embodiment of a method of the invention shows that rAAV productivity in B-50 cells infected with Ad5wt and AdAAV hybrid virus demonstrated that Ad5wt infection of B-50 cells prior to rAdAAV infection produces a high yield (i.e., greater than $1\times10^3$ virus particles to greater than $1\times10^6$ virus particles) of infectious rAAV. Such yields are between greater than 2-fold to greater than 20 fold the reported yields of the prior art methods.

The temporal relationship between rep/cap induction and AAV rescue and replication as well as infectious dose, i.e., the multiplicity of infection (MOI) of the helper and AdAAV hybrid viruses, can be readily adjusted to optimize rAAV production, depending on the cell line, helper and AdAAV hybrid used. Such adjustments are accomplished by performing experiments varying the times of infection and MOIs, such as those described above and reported in FIG. 2A and 2B. In the embodiments described in FIG. 2A, for example, these experiments varying the time between infection of the wild type and hybrid viruses demonstrated a substantial increase in rAAV production with maximal yields obtained, when B50 cells were infected with hybrid virus 24 hours after the helper (see, e.g., FIG. 2A).

The method of this invention utilizing endogenous AAV promoters in the host cell line in combination with an E1 expressing, helper adenovirus simulates the biology of a wild type AAV infection. Presently, desirable conditions for rAAV production using the B-50 cell line, wildtype adenovirus and the Ad.AAVCMVLacZ hybrid virus as the cis-acting vector include the following:

(a) infect B-50 cells with Ad5wt at a MOI of at least 5. An MOI of 10 is also desirable, although the less wildtype adenovirus employed in the method, the easier is the purification of rAAV from helper) for between 12 to 24 hours. As shown above for this embodiment, 24 hours appears to be most desirable to enhance rAAV yield;

(b) infect the cells with the hybrid Ad.AAVCMVLacZ virus at an MOI of at least 5 for an additional 36 hours. One of skill in the art given the teachings of this invention can easily adjust these dosage and infection timing parameters to provide optimal conditions for other embodiments of this invention employing other cell lines than B-50, other hybrid viruses and other helpers. The performance of the tests to determine optimal production conditions do not involve any degree of undue experimentation.

EXAMPLE 4

Recombinant AAV Product by the Hybrid Virus is Free of Replication Competent AAV The traditional method for producing rAAV frequently yields replication competent AAV (rcAAV) through nonhomologous recombination that occurs during the transient transfection. This example demonstrates that formation of rcAAV is decreased by using the production method of this invention, because the transfected rep/cap genes in the chromosomal DNA of the cell line of the invention are sequestered from the adenovirus encoded AAV vector DNA of the hybrid virus.

A. Production and Purification of rAAV rAAV was generated by plasmid transfection of the cis plasmid (i.e., which carries the AAV cassette) and trans plasmid (i.e., which carries the rep/cap genes) in 293 cells infected with E1 deleted adenovirus and isolated following heat denaturation and CsCl gradient purification, as described by Fisher et al, *Nature Med.* 3:306–312 (1996). Alternatively, rAAV was produced using the B50 cell line and AdAAV hybrid virus according to the method of this invention. B50 cells seeded in 150 mm² plates at a density of $1\times10^7$ cells per plate were infected with either wild type Ad5 or sub100r virus [Schaack, cited above; i.e., a temperature sensitive mutation in E2b30] at an MOI of 10 to 24 hours, and then with the AdAAV hybrid vector at the same MOI for an additional 48 hours. The cells were harvested for rAAV preparation and CsCl gradient purification as described in Fisher, cited above.

Following the heat denaturation and CsCl centrifugation, the rAAV were subjected to several analyses. The total amount of rAAV genomes was quantitated by DNA hybridization as described by Fisher, cited above. Transducing titer was determined by exposing the AAV permissive cell line 84-31 to limiting dilutions of rAAV and analyzing the monolayer for foci of transgene expressing cells twenty-four hours later. Contaminating adenovirus was assessed by a plaque forming assay at a sensitivity of 1 adenovirus/$10^{11}$ rAAV genomes. No contaminating Ad was detected at these levels.

B. Assay for Contaminating rcAAV

The assay for replication competent AAV (rcAAV) is based on amplification of 293 cells in the presence of adenovirus through two passages followed by analysis of the resulting lysates for rep DNA by specific hybridization. Briefly described, the rAAV prep ($10^{10}$–$10^{11}$ genomes) is mixed with various quantities of wild type AAV (0 to $10^4$ genomes) in the presence or absence of wild type adenovirus at an MOI of 5 which was incubated with $5\times10^6$ 293 cells in a 100 mm² plate. The cells were harvested and total DNA was isolated for hybridization or the clarified crude lysates were prepared for a second round of amplification. After heat-inactivation of adenovirus at 56° C. for 1 hour, one-tenth of the crude lysate was inoculated in a fresh plate of 293 cells in the presence or absence of adenovirus for the second round of amplification. The cells were harvested 72 hours later and total DNA was prepared as the first amplification. Total DNA (10 μg) from the first and second amplifications was analyzed for rep sequences by DNA hybridization following digestion with HindIII endonuclease. The blot was hybridized to a $^{32}$P-labeled 2.7 kB HindIII/XbaI fragment of pAd/AAV containing cap sequence.

A sensitive contamination assay was developed to detect low level rcAAV in the presence of adenovirus to amplify the rcAAV. 293 cells in 100 mm$^2$ plates were infected with $10^1$, $10^2$, $10^3$, and $10^4$ genome copies of wild type AAV2 in the presence and absence of wild type Ad5 at an MOI of 5 for 72 hours. Assays were also performed in the presence of 293 cell lysate to evaluate possible interference in the assay. Total DNAs were prepared from two-thirds of the infected cells. The other one-third of cells were lysed in the infection medium by three rounds of freezing/thawing and one-fifth of each lysate was heat-inactivated for the second amplification in 293 cells for another 72 hours. After this second passage, total DNAs were extracted again. The lysate is evaluated for rep DNA by Southern blot hybridization analysis as follows: total DNA (10 μg) digested with HindIII was fractionated, blotted and probed with a 2.7 kb Cap specific fragment. Analysis of DNA following the first and second amplification was shown in the resulting autoradiograms (not shown). Digestion of the trans plasmid with XbaI/HindIII releases a fragment that comigrates with the amplified and restricted rcAAV. This assay detects as little as 10 wild type AAV genomes. Similar levels of rcAAV contamination were observed in transfection experiments in which the trans plasmid was modified to minimize recombination or when the adenovirus helper was replaced with an Ad plasmid (data not shown).

Detection of rcAAV in large scale production lots was made as follows: $2\times10^{10}$, $2\times10^9$, and $2\times10^8$ genome copies each of two purified rAAV stocks were used for 1 round of amplification in 293 cells. rAAvlacZ was produced by 293/cotransfection, whereas rAAVGFP was produced by B50 hybrid system. The analysis of the first round amplified lysate was made in an autoradiogram (not shown). Analysis of rAAV produced by 293/cotransfection methodology consistently demonstrated rcAAV at levels equivalent to $1/10^3$–$10^6$ of the total rAAV preparation; no rcAAV ($<1/10^9$) was detected from rAAV preparations made by the method of this invention employing the B50 cell line and hybrid AdAAV. No rcAAV was seen following another round of amplification.

Sensitivity of the contamination assay in the presence of vector as assessed by spiking stocks of rAAV produced by the method of this invention using B-50 and with limiting quantities of wild type AAV. To determine the potential interference of rAAV genomes on the detection of rcAAV, 1, $10^1$, $10^2$, $10^3$, and $10^4$ genomes of wild type AAV were spiked into either $2\times10^{10}$ or $2\times10^{11}$ genomes each of rAAVGFP produced by B50/shuttle virus system for 2 rounds of amplification. Total DNA was extracted from the infected cells (10 μg) of the second rounds amplifications and digested with HindIII prior to Southern blot analysis. As little as 10 wild type AAV genomes can be detected in $2\times10^{10}$ rAAV genomes, although the sensitivity of the assay for detection of contaminating rcAAV is reduced in the presence of 10-fold higher AdAAV vector. The final preparations contained less than 1 transducing adenoviral particle per $10^{11}$ AAV genomes.

EXAMPLE 5

IN VIVO Use of rAAV Produced by the Hybrid Virus

A comparative study of rAAV preparations was performed by introducing rAAV expressing either rhesus monkey Epo or lacZ into skeletal muscle of mice. In this experiment, intramuscular injection of AAV vector encoding erythropoietin into skeletal muscle of mice resulted in supraphysiologic levels of hormone in serum that was stained and caused polycythemia.

More particularly, recombinant AAV expressing rhesus monkey Epo or lacZ from a CMV promoter was analyzed in either immune deficient mice (i.e., Rag1$^{-/-}$) or immune competent mice (C57BL/6) as follows. C57BL/6 or Rag$^{-/-}$ mice (4/group) were injected with $1\times10^{11}$ genome copies/50 μl of rAAV-Epo into the tibialis anterior muscle. The rAAV-Epo was produced according to the standard 293/cotransfection method or according to the method of this invention employing the B50 cell line and the AdAAV hybrid.

Figure 3A:
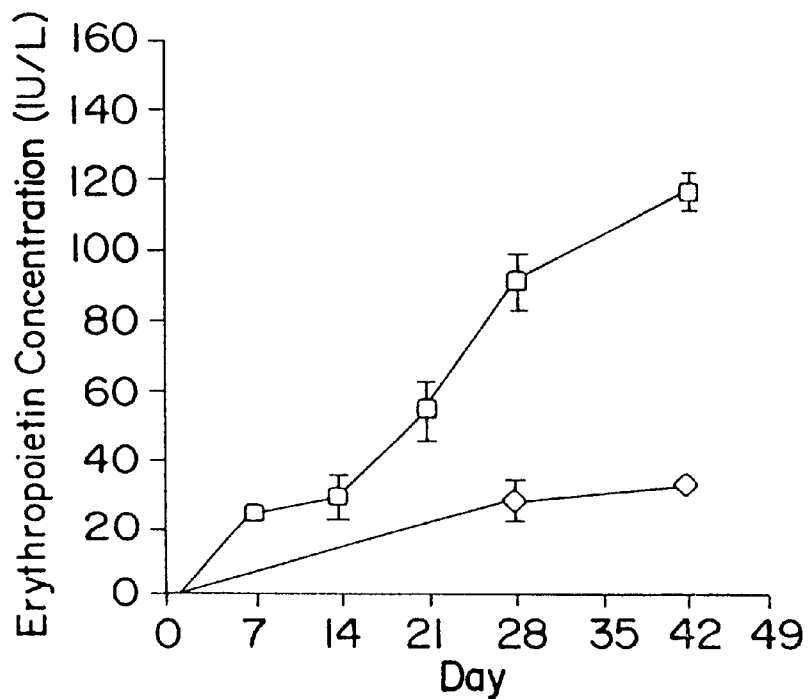
FIG. 3A is a graph showing the analysis of mice following infection of a rAAV carrying an erythropoietin gene (AAV-Epo) into skeletal muscle as described in Example 5. Mice received AAV-Epo derived from conventional 293/ cotransfection (squares) or AAV-Epo derived from use of one embodiment of a cell line of this invention and a method of this invention (triangles). Epo levels are measured as 1 $\mu$/L.
Figure 3B:
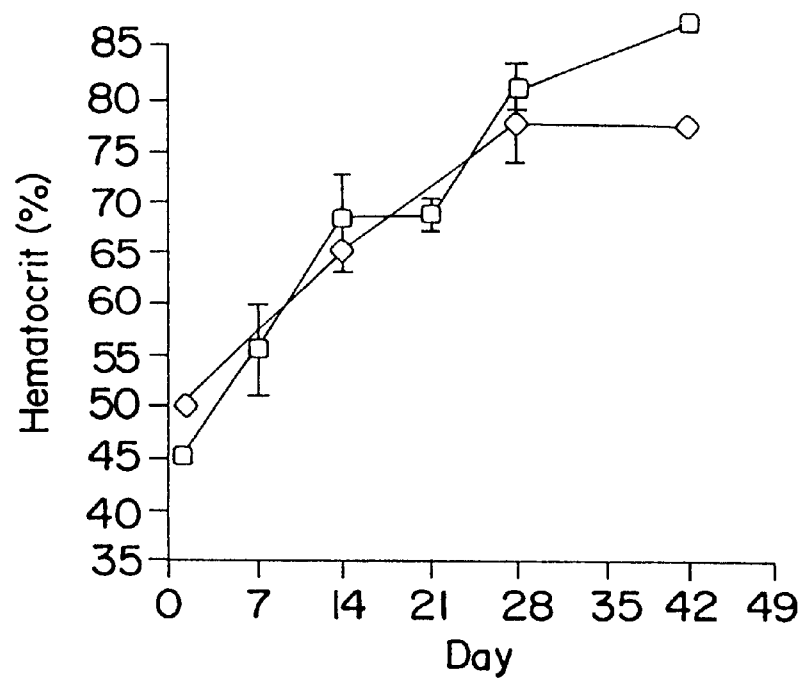
FIG. 3B is a graph measuring the hematocrits as % blood volume for animals treated as described in Example 5.

Serum from the rAAV-Epo injected animals was harvested and analyzed for virus derived Epo using commercially available ELISA (Quantikine IVD, R & D Systems) that cross-reacts with rhesus monkey Epo. Recombinant human erythropoietin served as a standard. Hematocrits were determined using microcapillary tables followed by centrifugation in an IEC Micro-MB centrifuge. Equivalent doses ($1\times10^{11}$ genomes) of each rAAV-Epo preparation yielded similar elevations in hematocrit, although the B50/hybrid rAAV-Epo vector yielded 4-fold more serum Epo than the rAAV-Epo vector derived from 293/co-transfection. See, e.g., FIGS. 3A and 3B. The B50/hybrid produced rAAV-Epo was more infectious that the rAAV-Epo produced by the conventional method.

Mice received various preparations of rAAV-lacZ by direct injection into the tibialis anterior, i.e., 293/co-transfection ($1.7\times10^{10}$ genome copies) and B50/hybrid ($1.7\times10^{10}$ genome copies or $3.8\times10^{10}$ genome copies or $1.7\times10^{11}$ genome copies). Skeletal muscle was harvested five weeks later and evaluated for β-galactosidase expression using X-gal histochemistry. Identical levels of X-gal staining in the tibialis anterior were seen 4 weeks after immunocompetent mice were injected with $1.7\times10^{10}$ genomes of vector derived from the B50/hybrid and 293/co-transfection methods. Increasing the dose of the lacZ vector produced by the B50/hybrid method yielded a proportional increase in β-galactosidase staining without evidence of inflammation (data not shown). For example, infection with $1.7\times10^{10}$ genome copies yielded from a visual inspection of the gel, about 5% stained muscle fiber. In comparison, infection with $1.7\times10^{11}$ genome copies yielded from a visual inspection of the gel, about 50% stained muscle fiber. Similarly a 3-fold increase in genome copies from the 5% baseline, yielded about 15% stained muscle fiber.

All documents cited above are incorporated by reference herein. Numerous modifications and variations of the present invention are included in the above-identified specification and are expected to be obvious to one of skill in the art. Such modifications and alterations to the processes of the present invention are believed to be encompassed in the scope of the claims appended hereto.

What is claimed is:

1. A stable cell useful for production of recombinant adeno-associated virus (AAV), said cell transformed with at least five copies of a nucleic acid molecule stably integrated into the cell's genome, wherein said molecule contains AAV sequences consisting essentially of AAV rep gene, an AAV cap gene, and regulatory sequences which direct expression of the rep and cap genes, said regulatory sequences comprising AAV P5 which is located in the native AAV position upstream of the AAV rep gene and directs expression of the rep genes upon activation with an exogenously introduced helper.

2. The cell according to claim 1, wherein the rep and cap genes are operatively linked to separate regulatory sequences.

3. The cell according to claim 1, wherein the rep and cap genes are operatively linked to the same regulatory sequences.

4. The cell according to claim 1, wherein the rep and cap genes are derived from different serotypes of AAV.

5. The cell according to claim 1, wherein the AAV P5 promoter is derived from a different AAV serotype than the rep and cap genes.

6. A B-50 cell having ATCC Accession No. CRL 12401.

7. The cell according to claim 1, wherein the helper is a member selected from the group consisting of an adenovirus, a herpes virus, a recombinant adenovirus, a recombinant herpes virus, an adenovirus gene, a herpes virus gene, an adenovirus gene product, and a herpes virus gene product.

8. A method for producing a helper-containing host cell, said method comprising the step of:

(a) introducing to a host cell, said cell transformed with at least five copies of a nucleic acid molecule stably integrated into the cell's genome, wherein said molecule contains AAV sequences consisting essentially of an AAV rep gene, an AAV cap gene, and regulatory sequences which direct expression of the rep and cap genes, said regulatory sequences comprising AAV P5 which is located in the native AAV position upstream of the AAV rep gene and directs expression of the rep genes upon activation with an exogenously introduced helper, and wherein the helper is selected from the group consisting of a helper virus, a helper gene, and a helper gene product.

* * * * *